United States Patent [19]

Hilaire et al.

[11] Patent Number: 4,831,061
[45] Date of Patent: May 16, 1989

[54] POLYAMIDE POWDER FORMED BY PARTICLES HAVING A GYPSUM ROSE STRUCTURE AND PROCESS FOR PREPARING SUCH POWDER

[75] Inventors: Jean-Claude Hilaire; Roland Guerin, both of Pau, France

[73] Assignee: Atochem, France

[21] Appl. No.: 217,557

[22] Filed: Jul. 11, 1988

[30] Foreign Application Priority Data

Aug. 11, 1987 [FR] France .................. 87 11422

[51] Int. Cl.$^4$ .............................. C08J 9/28
[52] U.S. Cl. ...................... 521/56; 521/64; 521/183; 521/189; 528/315
[58] Field of Search ............... 521/183, 189; 528/315

[56] References Cited

U.S. PATENT DOCUMENTS

| | | | |
|---|---|---|---|
| 3,917,761 | 11/1975 | Scheuerlein et al. | 521/185 |
| 4,444,911 | 4/1984 | Worota et al. | 521/184 |
| 4,506,037 | 3/1985 | Suzuki et al. | 521/82 |
| 4,520,071 | 5/1985 | Noda et al. | 521/184 |
| 4,552,810 | 11/1985 | Worota et al. | 521/184 |
| 4,595,746 | 6/1986 | Gabbert et al. | 528/315 |
| 4,595,747 | 6/1986 | Gabbert | 528/315 |
| 4,599,398 | 7/1986 | Hodek et al. | 528/315 |
| 4,716,215 | 12/1987 | Matsui et al. | 521/185 |
| 4,746,724 | 5/1988 | Nap et al. | 528/315 |

*Primary Examiner*—Morton Foelak
*Attorney, Agent, or Firm*—Sigalos, Levine & Montgomery

[57] ABSTRACT

A polyamide powder consisting essentially of elementary porous particles having a "gypsum rose" structure and a process for preparing a polyamide powder comprising polymerizing by anionic polymerization lactam in a solvent medium in the presence of a catalyst, an activator, and at least one amide; one of which is N,N'-alkylene bisamide; said polymerization being initiated with said lactam and said amide used in an amount such that the solvent is in the supersaturated state at the polymerization initiation temperature.

7 Claims, 1 Drawing Sheet

4,831,061

POLYAMIDE POWDER FORMED BY PARTICLES HAVING A GYPSUM ROSE STRUCTURE AND PROCESS FOR PREPARING SUCH POWDER

BACKGROUND OF THE INVENTION

The present invention pertains to a polyamide powder formed by porous elementary particles having a "gypsum rose" structure. The particularity of these particles is that they have a high absorption capacity due to the high number of pores and the large pore volume. These properties of the particles consequently lead to a polyamide powder of a large specific surface and low apparent density.

The polyamide powder is prepared by anionic polymerization of lactam in a solvent medium in the presence of at least one alkylene amide. The structural particularity of the particles is achieved by initiating the polymerization in a solvent medium which is supersaturated with lactam at the initiation temperature.

A process for manufacturing a polyamide powder by anionic solution polymerization of lactam in the presence of an alkylene bisamide is described in French Patent No. 2,576,602. According to the technique disclosed in this patent, which consists of dissolving the total amount of the lactam in the solvent in the presence of an alkylene bisamide prior to the polymerization initiation, powders with controlled particle size composition and controlled molecular weight are obtained. The particles obtain have a small specific surface (below 9 m²/g) and consequently a very low porosity.

SUMMARY OF THE INVENTION

In contrast, the elementary porous particles of the powder according to the present invention have an essentially spheroidal spongy structure in the form of a "gypsum rose". The "gypsum rose" structure is defined, in mineralogical analogy to the desert rocks thus called, as particles having a lamellar or shell-like structure whose lamellae, which grow anarchically and are connected to each other, form cavities whose geometric shapes vary between the conical and pyramidal shapes, and the apices of these geometric forms are directed toward the center of the particle. The walls of the cavities, having marked borders, generally have thicknesses smaller than 0.2 micron, the thickness of the middle lamella forming these walls being generally even smaller than 0.1 micron.

The invention also comprises the process of making such powders as hereinafter set forth.

DETAILED DESCRIPTION

Figure 1:
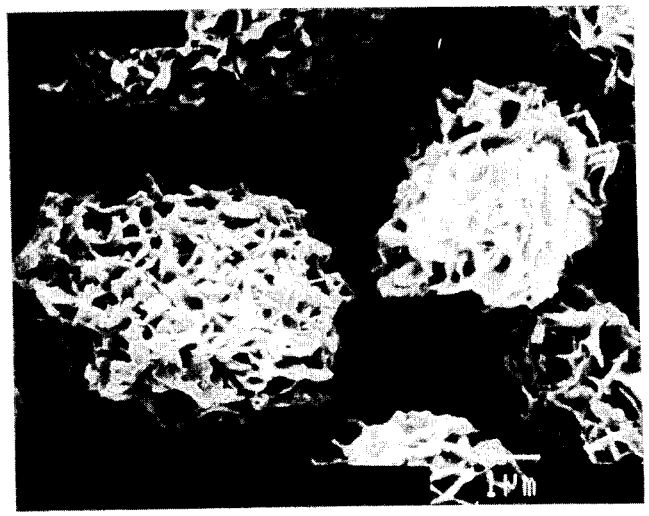
FIG. 1 is a photomicrograph of the polyamide powder particles of the present invention made in accordance with Example 1 hereof.

These spheroidal elementary particles have a mean diameter between 1 and 20 microns, usually between 2 and 10 microns. They are characterized in that they have a large pore volume. The internal pore volume in the particles is generally larger than 0.3 cm³/g, most often larger than 1 cm³/g in the range of median pore radii between 0.02 and 0.4 micron. If the cavities as defined above resemble cylinders, the median pore radius of these particles is usually between 0.09 and 0.16 micron. The pore volume is determined by mercury penetration under variable pressures according to Washburn's law:

$$R = \frac{2\gamma \cos\theta}{P}$$

R = radis of the cylindrical pore
$\gamma$ = interfacial tension between the Hg and the solid
$\theta$ = wetting angle between the liquid and the solid
P = penetration pressure of the Hg
(*Proc. Nat. Acad. Sci. USA* 7, 115 (1921)).

Due to the number and the value of the pores of the elementary particles forming the powder, the latter has a specific surface larger than 9 m²/g, very often between 9 and 30 m²/g. This specific surface is determined according to the classical BET method.

Due to their structure, the elementary particles also have a very high absorption capacity. This novel property is characterized in that the powder formed by these elementary particles absorbs at least 90%, generally more than 120%, of its weight of linseed oil. The absorption values are determined according to the ASTM D 281-31 standard which pertains to the oil absorption of pigments. This absorption characteristic is of particular interest in the area of cosmetics, analgesics, pharmaceutics, microencapsulation, etc., where absorption of adjuvants is desirable, e.g., in the case of cosmetology (for beauty powders) or in the analgesic industry where it is desirable to incorporate the largest possible amount of active analgesic ingredients in a minimum amount of carrier.

This very high absorption capacity is associated with the slowness of desorption. The observation of the latter phenomenon increases the interest in powders containing these specific particles for the above-mentioned applications.

The polyamide powder initially formed by these particles generally contains at least 90 wt. %, most often 95 wt. %, particles possessing the characteristics as defined above. Another characteristic of the powder is that it has a narrow particle size distribution. This particle size distribution can be determined with a Coulter counter according to the standards NF×11-670 and 671. It is possible to calculate the $d_{50}$ diameters as well as the $d_{84.14}$ and $d_{15.87}$ diameters, which correspond to a standard deviation in either direction from the median of $d_{50}$, from the cumulative frequency curve of decreasing diameters. The particle size range or the particle size dispersion is defined by the ratio $\sigma^2 = d_{16}/d_{84}$.

The particle size dispersion of the powder is usually between 1.2 and 2.5. Due to the considerable porosity of the particles, the polyamide powder has a low apparent density. According to the standard ISO R787/11, the apparent density of the nonpacked powder is between 0.12 and 0.22, and the packed apparent density is between 0.22 and 0.30.

The process for preparing the polyamide powders is, in general, a conventional process. It is based on the anionic polymerization of lactams, which is principally based on the use as the catalyst of an alkali metal or its compounds such as sodium or one of the compounds sodium hydride or sodium methylate. An activator selected, e.g., from among the N-carboxyanilide lactams, isocyanates, carbodiimides, cyanimides, acyl lactams, triazines, ureas and N-substituted imides is also used in this type of polymerization.

The lactams used as monomers preferably are, according to the state of the art of the industry, lauryl lactam, caprolactam, enantholactam and capryl lactam or mixtures thereof.

The polymerization of the lactams is carried out, likewise in the known manner, in a solvent medium which is inert with respect to the components of the reaction and to the reaction mechanism, in the presence of at least one amide, one of which is always an N,N'-alkylene bisamide.

The N,N'-alkylene bisamides which are particularly recommended include N,N'-alkylene bisamides of fatty acids, especially:

N,N'-ethylene-bis-stearamide of the formula of

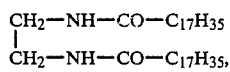

N,N'-ethylene-bis-oleamide of the formula of

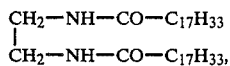

N,N'ethylene-bis-palmitamide, gadoleamide, ceto leamide and erucamide, N,N'-dioleyl adipamide and N,N'-dierucylamide.

The amount of N,N'-alkylene bisamide used is on the order of magnitude of about 0.001 to 4 moles, especially 0.075 to 2 moles, per 100 moles of lactam.

The purpose of adding N,N'-alkylene bisamide to the reaction medium is to cause the reaction to slow down to produce a powder of a very narrow particle size distribution without soiling the reactor.

All the lactam solvents are suitable for the reaction medium providing that they are inert with respect to the reagents and do not participate in the polymerization reaction. The most frequently used solvent, ssentially for economic reasons, is a paraffin hydrocarbon fraction, which is a mixture of isoparaffin, n-paraffin and cycloparaffin, which boils in the range between 140° C. and 170° C. However, to obtain the particles and the powders according to the present invention, the isoparaffins which preferably contain 6 to 12 carbon atoms in their molecules are particularly recommended. The boiling point of these isoparaffins is, in general, at least 120° C.

Compared to other processes, the process according to the present invention is distinguished therefrom in that the solvent polymerization is initiated with such an amount of lactam and amide that the solvent is in the supersaturated state at the initiation temperature.

The solvent in the reaction medium can be supersaturated with lactam in various manners. One method can be to saturate the solvent with lactam and amide before addition of the catalyst at a temperature that is higher than the initiation temperature, after which the temperature is lowered to initiate the polymerization.

Another method, which is the object of the present invention, is essentially to saturate the solvent with lactam and amide at the polymerization initiation temperature and to add a primary amide to the reagents before the initiation to reduce the solubility of the lactam. This primary amide, which preferably contains 12 to 22 carbon atoms in its molecule, may be chosen from among oleamide, N-stearamide, isostearamide and erucamide. The amount of the primary amide to be mixed with the other reagents is preferably lower than 0.5 mole per 100 moles of lactam.

The limits of the solvent supersaturation are not critical. The lower limit may be such that if the medium is in the monophasic but metastable state at the initiation temperature, it is sufficient to add a few crystals of one of the reactive components which are soluble in the solvent to case the medium to turn turbid. Th polymerization may also be initiated from a biphasic medium, a portion of excess lactam being in the solid state in the medium. Under these conditions, the excess lactam is dissolved in the medium before polymerization as the precipitation of the polyamide particles formed progresses.

As an example, the polymerization may be carried out in the conventional manner by contacting with each other, in a reactor, the solvent and the lactam and amide used in such an amount that the solvent will be in the supersaturated state at the subsequent polymerization initiation temperature.

Since any trace of moisture is to be prohibited during the polymerization, it is recommended that perfectly anhydrous reagents should be used or that they should be dried in any known manner before the initiation of the polymerization.

The mixture is brought to the initiation temperature, preferably while stirring and under an inert atmosphere, after which the anionic catalyst and the activator are added simultaneously or separately, all at once or gradually.

The amount of catalyst introduced may range from 0.8 to 3 moles per 100 moles of lactam. The percentage of activator introduced may range from 2 to 8 moles per 100 moles of lactam.

The initiation temperature and the polymerization temperature of the lactams is generally between 80° C. and 130° C., the most frequently used temperature being close to 100° C.

It is possible to charge crystal seeds into the reaction medium. These crystal seeds are in the form of a finely divided charge. These charges may be organic, such as polyamide powder, preferably particles according to the present invention, which were prepared previously, or inorganic, such as silica or talc. It is important that this charge does not contain even trace amounts of water, and it must be carefully dehydrated especially if silica is used.

The present invention will be further described in connection with the following examples which are set forth for purposes of illustration only.

In these examples, the experiments were carried out in a five-liter reactor equipped with a blade-type stirrer, a double jacket in which heating oil circulates, a bottom discharge system, and a lock-chamber-type reagent charging system swept by dry nitrogen.

An azeotropic vacuum distillation device permits all traces of water to be removed from the reaction medium.

The solvent used is a paraffin hydrocarbon fraction which boils in the range of 130° C. to 160° C.

The particle size distribution and the mean particle diameter are measured with a Coulter counter.

The following abbreviations will be used for the sake of convenience:
  (i) EBS for N,N'ethylene-bis-stearamid,
  (ii) nST for n-stearamide, and (iii) iST for iso-stearamide.

EXAMPLE 1

3,040 ml of solvent are charged into the reactor maintained under a weak nitrogen current, and then, 1,087 g of dry lauryl lactam, 37.4 g of EBS, 0.55 g of nST and 4.3 g of finely divided and dehydrated silica are added.

After starting the stirring at 720 rpm, the temperature is gradually raised to 100° C., after which 200 ml of the solvent are distilled off under a vacuum of 26,660 Pa to azeotropically remove all traces of water that may still be present.

After returning to atmospheric pressure, the anionic catalyst, 1.95 g of sodium hydride with a purity of 80% in oil, is charged in rapidly under nitrogen, and the stirring is continued for 60 minutes, still under a nitrogen current.

The temperature is then brought to 100° C., and the activator selected (stearyl isocyanate) is continuously injected into the reaction medium by means of a small batching pump. The amount of isocyanate thus injected is 33 g within six hours, after which 21.8 g are injected within two hours. The temperature is maintained at the same time at 100° C. during the first six hours, after which it is raised to 110° C. and maintained there for three hours, or one hour after the end of the charging in of the isocyanate.

The polymerization is now terminated. The reactor is cooled to 90° C. and the powder slurry and the solvent are withdrawn from the bottom.

The centrifuging and drying, a polyamide 12 power with a particle size between 5.3 and 10.5 microns is obtained, the mean particle diameter being 8 microns. The nonpacked apparent density is 0.20, the packed apparent density is 0.27, and the BET specific surface is 9.4 $m^2/g$. The pore volume of the particles is 2.04 $cm^3/g$. The powder absorbs 180% of its weight of linseed oil.

The photograph of the product obtained is shown in FIG. 1.

EXAMPLE 2

The procedure is the same as in Example 1, but the solvent used is not a paraffin fraction; rather, it exclusively consists of $C_8$ to $C_{10}$ isoparaffins, which have a much lower dissolving power for the lauryl lactam. The powder obtained under these conditions has a particle size distribution between 4 and 8.6 microns and a "gppsum rose" structure. The BET specific surface is 10.2 $m^2/g$. The nonpacked apparent density is 00.18 and the packed apparent density is 0.26. The mean particle diameter is 5.8 microns, and the pore volume of the particles is 2.33 $cm^3/g$. The powder absorbs 220% of its weight of linseed oil.

Figure 2:
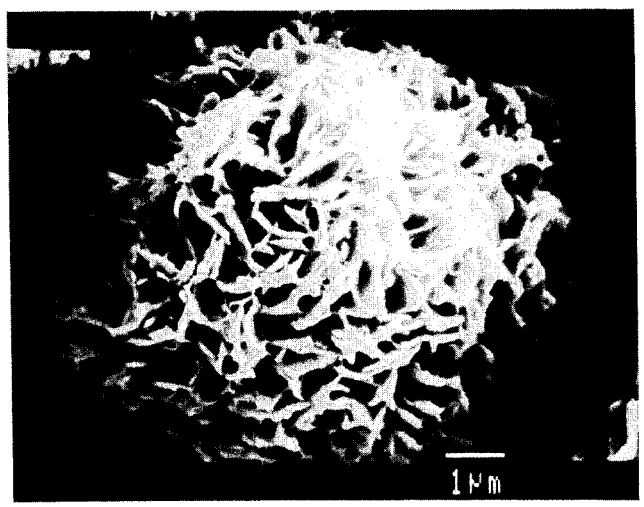
FIG. 2 is a photomicrograph of the polyamide powder particles of the present invention made in accordance with Example 2 hereof.

The photograph of the product obtained is shown in FIG. 2.

EXAMPLE 3

2,450 ml of solvent and then consecutively 873 g of lauryl lactam, 0.44 g of iST, 30 g of EBS and 17.4 g of silica are charged into the reactor.

The temperature is raised to 110° C. while stirring at 720 rpm, after which 200 ml of solvent are distilled off under a vacuum of 26,660 Pa. After returning to atmospheric pressure, 1.56 g of sodium hydride with a purity of 80% are charged in under nitrogen, and the mixture is maintained under a nitrogen atmosphere for 30 minutes. The temperature is lowered to 95° C., after which stearyl isocyanate is introduced by means of a small batching pump according to the following schedule:
  (i) 20 g of isocyanate within six hours at 95° C., and
  (ii) 30 g of isocyanate within two hours and 30 minutes at 110° C.

After completion of this charging, the temperature is maintained at 110° C. for one more hour. The reaction is then stopped. After cooling to 90° C., decantation and drying, the polyamide 12 powder has the following characteristics:
  (i) particle size between 3.4 and 7 microns,
  (ii) mean particle diameter: 5.3 microns,
  (iii) specific surface: 17 $m^2/g$,
  (iv) nonpacked apparent density: 0.14,
  (v) packed apparent density: 0.25,
  (vi) pore volume: 2.52 $cm^3/g$, and
  (vii) linseed oil absorption: 200 wt. %.

EXAMPLE 4

2,440 ml of solvent, 873 g of dodecalactam, 0.4 g of erucamide, 30 g of EBS and 17.5 g of silica are charged into the reactor. 200 ml of solvent are azeotropically distilled off under 26,660 Pa at 110° C. under the same conditions as in the preceding examples. The mixture is cooled to 100° C. and 1.71 g of 80% sodium hydride are added under nitrogen. After one hour, the stirring is adjusted to 720 rpm, and stearyl isocyanate is injected as follows:
  (i) 20 g of isocyanate within six hours at 95° C., and
  (ii) 30 g of isocyanate within two hours and 30 minutes at 110° C., after which the temperature is maintained at 110° C. for one hour.

After cooling and drying, a powder with a viscosity of 0.75, a particle size distribution of between 3.6 to 8 microns, a mean particle diameter of 5.4 microns and a BET specific surface of 15.6 $m^2/g$ is obtained.

The nonpacked apparent density is 0.17, and the packed apparent density is 0.26. The powder particles have the shape of "gypsum roses" and have a pore volume of 2.13 $cm^3/g$. The powder absorbs 200% of its weight of linseed oil.

EXAMPLE 5

3,040 ml of solvent and then consecutively 1,304 g of lauryl lactam, 45 g of EBS and 5.2 g of silica are charged into the reactor.

The temperature is raised to 110° C. while stirring at 720 rpm, after which 200 ml of solvent are distilled off under a vacuum of 26,660 Pa. After returning to the atmospheric pressure, 2.34 g of 80% sodium hydride are charged in under nitrogen, and the nitrogen atmosphere is maintained for 30 minutes at 110° C. The temperature is then lowered to 100° C. Stearyl isocyanate is then gradually charged in as follows:
  (i) 30 g of isocyanate within six hours at 100° C., and
  (ii) 36 g of isocyanate within two hours at 110° C., and the temperature is maintained at 110° C. for one hour.

After cooling to 90° C., decantation and drying, a polyamide 12 powder is obtained having the following characteristics:
  (i) particle size between 4.8 and 9.3 microns,
  (ii) mean particle diameter: 6.7 microns,
  (iii) BET specific surface: 9.3 $m^2/g$,
  (iv) nonpacked apparent eensity: 0.20,
  (v) packed apparent density: 0.29,
  (vi) pore volume: 2.07 $cm^3/g$, and
  (vii) linseed oil absorption: 180 wt. %.

The powder particles have the shape of "gypsum roses".

EXAMPLE 6

2,240 ml of solvent and then consecutively 1,087 g of caprolactam, 18.7 g of EBS and 21.9 g of silica are charged into the reactor. The mixture is then heated to 110° C. as above while stirring at 720 rpm, after which 300 ml of solvent are distilled off under a vacuum of 26,660 Pa.

After returning to atmospheric pressure, 8.3 g of 80% sodium hydride are charged in under nitrogen, and the nitrogen atmosphere is maintained at 110° C. for 30 minutes. The temperature is then lowered to 80° C. The progressive charging of 41.6 g of stearyl isocyanate within four hours at 80° C. is then started, after which the temperature is raised from 80° C. to 130° C. within two hours, and the mixture is maintained at 130° C. for two hours. After cooling to 90° C., decantation and drying, a polyamide 6 powder is obtained at 100% yield having the followingccharacteristics:

(i) "gypsum rose" structure,
(ii) particle size distribution between 3.6 and 7.2 microns,
(iii) mean particle size: 5.0 microns,
(iv) BET specific surface: 9.9 m$^2$/g,
(v) pore volume: 1.21 cm$^3$/g, and
(vi) linseed oil absorption: 170 wt. %.

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. A process for preparing a polyamide porous powder of having a "gypsum rose" structure wherein the particles have a lamellar or shell-like structure whose lamellae, which grow anarchically are connected to each other, form cavities whose geometric shapes vary between the conical and pryamidal shapes, and the apices of these geometric forms are directed toward the center of the particle, comprising polymerizing by anionic polymerization lactam in a solvent medium in the presence of a catalyst, an activator, and at least one amide; one of which is N,N'-alkylene bisamide; said polymerization being initiated with said lactam and said amide used in an amount such that the solvent is in the supersaturated state at the polymerization initiation temperature.

2. The process of claim 1, wherein the solvent is an isoparaffin.

3. The process of claim 2, wherein a primary amide is added to the reaction medium before the polymerization is initiated.

4. The process of claim 3, wherein the primary amide contains 12 to 22 carbon atoms.

5. The process of claim 4, wherein the amount of N,N'-alkylene bisamide used is between 0.001 and 4 moles per 100 moles of lactam.

6. The process of claim 5, wherein the amount of the primary amide used is lower than 0.5 mole per 100 mole of lactam.

7. The process of any one of claims 1 through 6, wherein the polymerization initiation temperature is between 80° C. and 130° C.

* * * * *

UNITED STATES PATENT AND TRADEMARK OFFICE
CERTIFICATE OF CORRECTION

PATENT NO. : 4,831,061
DATED : May 16, 1989
INVENTOR(S) : Hilaire et al.

It is certified that error appears in the above-identified patent and that said Letters Patent is hereby corrected as shown below:

Column 8, line 5, cancel the word "of".

Signed and Sealed this

Twenty-eighth Day of November 1989

Attest:

JEFFREY M. SAMUELS

Attesting Officer     Acting Commissioner of Patents and Trademarks